United States Patent
Browner et al.

(10) Patent No.: US 6,571,632 B1
(45) Date of Patent: Jun. 3, 2003

(54) METHOD AND APPARATUS TO PROVIDE DYNAMIC ULTRASONIC MEASUREMENT OF ROLLING ELEMENT BEARING PARAMETERS

(75) Inventors: Richard W. Browner, Waterbury, CT (US); Richard L. Lemoine, Collinsville, CT (US); Mark I. Jurras, III, Canton Center, CT (US); David Nguyen, Farmington, CT (US); Robert Domnitz, Lexington, MA (US); Alan Robert Selfridge, Los Gatos, CA (US)

(73) Assignee: The Torrington Company, Torrington, CT (US)

( * ) Notice: Subject to any disclaimer, the term of this patent is extended or adjusted under 35 U.S.C. 154(b) by 0 days.

(21) Appl. No.: 09/573,644

(22) Filed: May 18, 2000

(51) Int. Cl.[7] .......................... G01M 13/04; G01N 29/18
(52) U.S. Cl. .......................................... 73/593; 73/597
(58) Field of Search .................... 73/587, 579, 593, 73/660, 659, 597, 598, 599, 600

(56) References Cited

U.S. PATENT DOCUMENTS

| | | | | |
|---|---|---|---|---|
| 3,812,709 A | * | 5/1974 | Benson et al. ............... 73/67.5 |
| 4,080,836 A | * | 3/1978 | Thompson et al. ........... 73/597 |
| 4,210,028 A | * | 7/1980 | Hildebrand ................... 73/598 |
| 4,763,523 A | | 8/1988 | Womble et al. ............... 73/587 |
| 4,926,692 A | * | 5/1990 | Brokowski et al. ........... 73/597 |
| 5,195,372 A | | 3/1993 | Fushimi et al. ............... 73/593 |
| 5,257,544 A | | 11/1993 | Khuri-Yakub et al. ........ 73/579 |
| 5,398,551 A | | 3/1995 | Kawasaki et al. ............. 73/593 |
| 5,433,525 A | | 7/1995 | El-Ibiary ...................... 374/141 |
| 5,499,540 A | | 3/1996 | Whaley et al. ................ 73/761 |
| 5,602,539 A | | 2/1997 | Lemoine et al. ....... 340/870.16 |
| 5,642,105 A | | 6/1997 | Duffy et al. ........... 340/870.17 |
| 5,677,488 A | | 10/1997 | Monahan et al. ............. 73/593 |
| 5,691,707 A | | 11/1997 | Smith et al. ................. 340/682 |
| 5,750,900 A | * | 5/1998 | Hugentobler et al. ......... 73/779 |
| 5,804,727 A | * | 9/1998 | Lu et al. ....................... 73/597 |
| 6,009,380 A | * | 12/1999 | Vecchio et al. ............. 702/142 |

FOREIGN PATENT DOCUMENTS

| | | | |
|---|---|---|---|
| EP | 0 228 731 B1 | 6/1991 | |
| EP | 0 856 733 A1 | 8/1998 | |
| JP | 6025733 | * 12/1985 | .................. 73/760 |
| JP | 401291135 A | * 11/1989 | .................. 73/620 |
| JP | 2000275122 | * 10/2000 | |

* cited by examiner

*Primary Examiner*—Hezron Williams
*Assistant Examiner*—Rose M. Miller
(74) *Attorney, Agent, or Firm*—John C. Bigler (57) ABSTRACT

An acoustic signal unit comprises a signal generation unit to generate a first electrical signal, a first transducer to generate an acoustic signal in response to the first electrical signal, and a second transducer to generate a second electrical signal in response to the received acoustic signal. A calculation unit is provided to compare the first and second electrical signals to determine the time of flight of the acoustic signal, wherein the time of flight corresponds to the stress in the rolling element bearing. The stress may be calculated according to a formula or by multiplying an acoustic time constant for the rolling element bearing by the distance traveled by the acoustic signal across the rolling element bearing, and by the time of flight determined by said comparison unit.

20 Claims, 10 Drawing Sheets

METHOD AND APPARATUS TO PROVIDE DYNAMIC ULTRASONIC MEASUREMENT OF ROLLING ELEMENT BEARING PARAMETERS

BACKGROUND OF THE INVENTION

The present invention relates to a method and apparatus to detect multiple operating parameters in rolling element bearings. More particularly, the present invention relates to a method and apparatus to detect real time dynamic stress in rolling element bearings by way of an ultrasonic measurement system. The present invention further relates to a method and apparatus to detect rolling element bearing temperature and speed using the same ultrasonic measurement system.

Traditionally, rolling element bearing life has been predicted by applying a predetermined load to the rolling element bearing, and operating the bearing to a point of failure. Statistical averaging has then been used to predict bearing life during operating conditions. While the relationship between load and bearing life is important, other factors more closely relate to the operational life of rolling element bearing components.

Stress is the response of a material to an applied load over an area. Stress is therefore an internal reaction between elementary particles of a material in resisting separation, compaction, or sliding that tend to be induced by an external force, i.e. load. Total internal resisting forces are resultants of continuously distributed normal and parallel forces that are of varying magnitude and direction and are acting on elementary areas throughout the material. Stress may be identified as tensile, compressive, or shearing, according to the straining action.

An elastic material under stress will strain, i.e. deform, according to the formula:

stress=(strain)×(modulus of elasticity)

By way of example, for bearing steels, the modulus of elasticity is approximately 30 million pounds per square inch and strain is reported in inches of deformation per inch of initial size.

Prior techniques have been applied to the non-operational measurement of bearing parameters. For example, Womble et al. set forth in U.S. Pat. No. 4,763,523 that a pair of solid state transducer probes may be manually positioned by a technician to determine defects in railcar axle bearings. A crack which develops in a bearing race emits an acoustic shock pulse when a rolling element crosses the crack. The shock pulse is then detected by the solid state transducer probes. Likewise, Bourgeois-Jacquet, et al. set forth in EP 0 856 733 A1 that ultrasonic sensors may be inserted into an inner or outer ring of a crane bearing to detect surface and subsurface damage which result from crane operation. A technique for determining an amount of pre-load which has been applied to a bolt by using an electromagnetic acoustic transducer has also been described by Whaley et al. in U.S. Pat. No. 5,499,540.

Methods have also been used to infer a load zone in rolling element bearings from calibrated strain gauge measurements, such as described by Rhodes, et al., U.S. Pat. No. 5,952,587, which is incorporated herein by reference. However, these methods require modification of the bearing in the locations where support for the applied load is required. In other words, material from the bearing must be removed to provide for placement of strain gauges. Moreover, strain measurement techniques are dependent upon a number of factors that can not be readily predictable, such as clearances in the system and the strength of the supporting structure.

The foregoing illustrates limitations known to exist in present devices and methods. Thus, it is apparent that it would be advantageous to provide an alternative directed to overcoming one or more of the limitations set forth above. Accordingly, a suitable alternative is provided including features more fully disclosed hereinafter.

SUMMARY OF THE INVENTION

In one aspect of the invention, this is accomplished by dynamically detecting stress in rolling element bearings by transmitting and detecting an ultrasonic wave. Rolling element bearing stress is non-invasively and non-destructively measured in situ, i.e. during bearing operation. Only very minor modifications to the bearing element are required and no degradation of load-bearing capacity is made through the removal of rolling element bearing material. Ultrasonic stress measurement provides significant improvement over strain gauge measurement. Time changes of an acoustic signal are measured rather than resistance changes of a strain gauge, to thereby reduce the problems associated with environmental factors, such as temperature, and variation in the resistance of the measurement circuit.

Stress is measured in a rolling element bearing with an acoustic signal unit which transmits and receives an acoustic signal across the rolling element bearing. The time of flight of the acoustic signal is determined and a stress calculation unit calculates stress in the rolling element bearing from the time of flight. A first transducer generates an acoustic signal in the rolling element bearing in response to a first electrical signal while a second transducer generates a second electrical signal in response to the received acoustic signal. The first and second electrical signals are then compared to determine a difference in time, which corresponds to a change in stress in the bearing. Stress is calculated in a rolling element bearing according to the formula: stress=K× L×Δt where K is the acoustic velocity stress constant for the rolling element bearing, L is the distance traveled by the acoustic signal across the bearing, and Δt is the time of flight of the acoustic signal.

The foregoing and other aspects will become apparent from the following detailed description of the invention when considered in conjunction with the accompanying drawing figures.

DETAILED DESCRIPTION OF THE PREFERRED EMBODIMENTS

Figure 1:
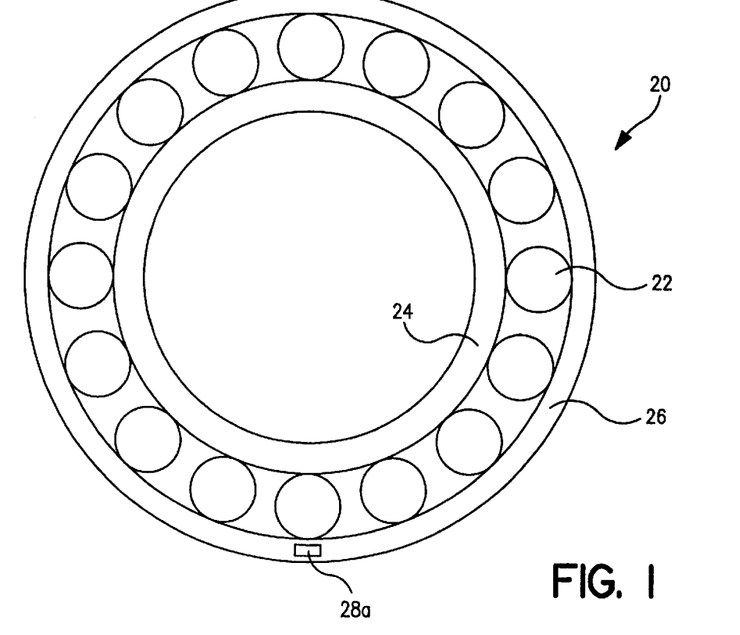
FIG. 1 is an elevated side view of a race for a rolling element bearing supporting an ultrasonic transducer.

Turning now to the drawings and more particularly to FIG. 1, where like numerals denote like components, a first embodiment providing dynamic ultrasonic measurement of parameters in rolling element bearings is shown and described.

FIG. 1 is an elevated side view of a rolling element bearing 20 having a plurality of rolling elements 22 disposed between an inner race 24 and an outer race 26. A first transducer 28a is disposed on a first face of outer race 26 while a second transducer 28b (not shown in FIG. 1) is disposed on a second face thereof.

As bearing 20 is loaded, the state of stress in each of the inner race 24 and the outer race 26 changes. Thus, the transducers may be mounted onto the inner or outer race, depending upon bearing application. In general, the transducers are preferably mounted onto a stationary race.

Figure 2:
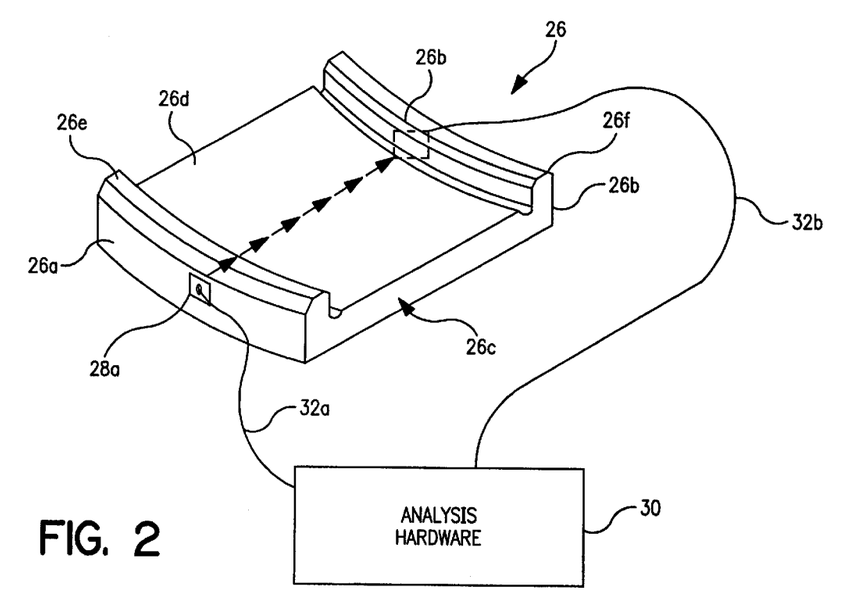
FIG. 2 is an elevated sectional view of an outer bearing race supporting a plurality of ultrasonic transducers.

FIG. 2 is an elevated sectional view of outer race 26 supporting ultrasonic transducers 28a and 28b. As illustrated, outer race 26 has a first face 26a provided as an outer surface of first lip 26e and a second face 26b provided as an outer surface of second lip 26f. Radial contact surface 26d is formed as an inner surface of radial web 26c. First transducer 28a is attached to first face 26a while second transducer 28b is attached to second face 26b. Each of the first and second transducers are electrically connected to pulse generation and analysis hardware 30 by way of electrical connectors 32a and 32b.

In general, an electrical pulse is used to excite transducer 28a, thereby generating an acoustic pulse. The time required for the acoustic pulse to be transmitted to and received on the opposing bearing face 28b is then measured as a time of flight. As a load is applied to the bearing, the resulting change in transmission time is recorded.

Transduce 38 is preferably an ultrasonic transducer in the form of a crystal exhibiting a strong piezoelectric effect. When excited by such an electrical signal, transducer 28a vibrates, causing an acoustic wave to be transmitted into the attached member, i.e. outer race 26. This acoustic wave then travels across the member and contacts second transducer 28b mounted on the opposing face. When the acoustic wave contacts the second transducer 28b, the transducer becomes excited mechanically, which then causes the transducer to generate an electrical signal similar to that applied to the first transducer. The time between the transmitted and received signals represents the time of flight through the member.

A compressive stress in the race increases the velocity of an acoustic signal in the steel, reducing the time of transmission across the race. Conversely, tensile stress increases the acoustic transmission time. This change in acoustic velocity is proportional to a change in stress over a wide range. In other words, as the compressive stress in the steel increases, the transmission time decreases proportional to the inverse of the magnitude of the stress.

The acousto-elastic property of a material is the phenomenon that causes the acoustic velocity of a sound wave transmitted through the material to vary with its state of stress. The present invention uses the acousto-elastic property of materials, and in particular the acousto-elastic property of steel, to determine stress in loaded bearing members. This velocity change is due to the introduction of anisotropy in the material that is isotropic in the free state.

Time of flight of an acoustic wave across a material is a practical way to determine an acoustic velocity in rolling element bearings, and therefore determine applied stress. A change in time of flight of an applied acoustic wave is produced by two phenomena occurring in the material simultaneously, namely: the change in velocity of the acoustic signal itself, and the change in distance traveled by the acoustic signal. The change in distance traveled is due to strain of the material in a direction perpendicular to the applied principal stress.

The Poisson strain is the strain in a material that is perpendicular to the applied stress. In this regard, the Poisson strain will cause the width of a bearing race to increase by approximately 0.3 times the amount of decrease in race thickness under an applied radial compressive stress. However, the increase in acoustic travel time due to the Poisson strain in the bearing race is approximately ¼ of the time change due to velocity increase. More importantly, these effects occur simultaneously and to the same extent, thereby being simultaneously incorporated into measured values.

Stress in rolling element bearings originates from contact between load bearing components, including the rolling elements, and inner and outer races. During normal operation, i.e. in the presence of adequate lubrication and under design loads, the level of stress in the load bearing components will most directly affect bearing life. The applied load gives rise to stress in the load bearing components through distribution among the rolling elements, which, through contact with the bearing races, transfer the applied load to the bearing housing and base. The applied load is eventually transferred to ground.

The useful life of rolling element bearing components is largely determined by stress. Through cyclical application of stress, the components experience a finite number of stress cycles before beginning to fatigue and, ultimately, fail to support the applied load. Lundberg and Palmgren predictions may be used to predict a number of stress cycles that a material can withstand. The Lundberg and Palmgren predictions suggest that the number of stress cycles is proportional to a ratio of design capacity to the applied load, raised to an exponent of 3 or 3⅓. The exponent used depends upon whether the rolling elements are balls or rollers, respectively.

Figure 3:
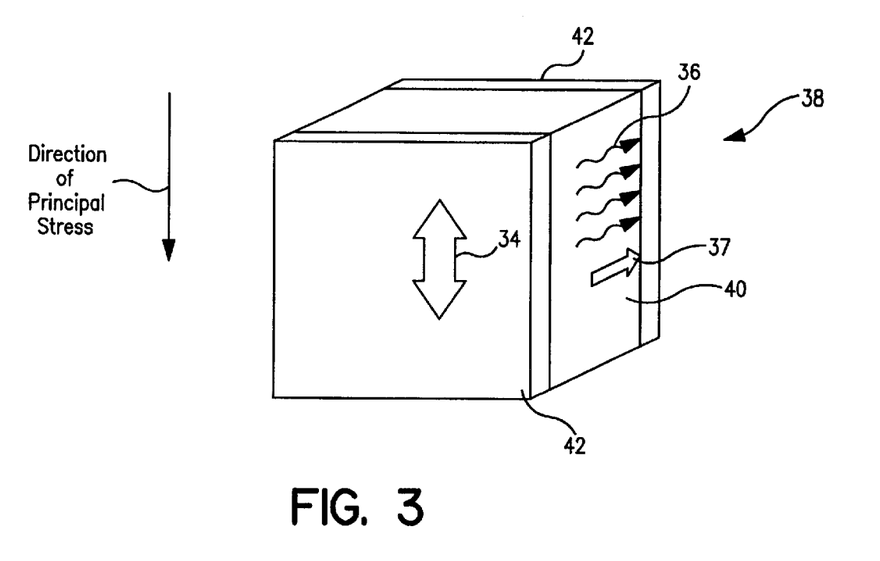
FIG. 3 is a schematic view of a lead zirconate titanate crystal, which exhibits piezoelectric properties.

FIG. 3 is a schematic view of an ultrasonic transducer 38, which may be used for first transducer 28a and second transducer 28b. Transducer 38 has a piezoelectric body 40 which is bonded to an electrode surface 42. Preferably, an ultrasonic wave is generated using a shear mode transducer. In other words, the transducer 38 is preferably polarized in a direction 34 which is perpendicular to the direction of the applied electric field 36, during excitation of the transducer.

Transducers 28a and 28b are preferably 0.180" square by 0.008" thick piezoelectric PZT crystals mounted to opposite sides of a bearing race. The transducers are affixed onto the race with an epoxy resin and an epoxy hardener. This epoxy essentially provides a zero-thickness film between the transducer and bearing face to obtain an electrical ground connection across surface asperities.

During manufacture of transducer 38, an electric field is applied in the direction of polarization 34. During operation of the transducer, a voltage is applied, which gives rise to electric field 36. As illustrated in FIG. 3, electric field 36 is transmitted in direction 37. In other words, transducer 38 is preferably polarized in a direction 34 which is perpendicular to the thickness of the transducer.

The polarization direction 34 determines the direction of particle motion in the generated acoustic wave. The transducer 38 vibrates in the polarization direction 34 perpendicular to the electric field 36, as illustrated. Transducer 38 is mounted on the bearing with the direction of polarization 34 parallel to the direction of principal stress, which essentially is the radial direction in the bearing. Therefore, the generated ultrasonic wave travels across the bearing with the direction of particle motion parallel to the applied radial load.

Of course, the acoustic wave does not travel in transducer 38 itself, rather, transducer 38 vibrates in the direction of polarization, which launches an acoustic wave in the material on which it is installed. This acoustic wave travels in the material in the direction 37 shown in FIG. 3.

When piezoelectric crystals are used to detect radial stress in rolling element bearings, radial stress is preferably measured using a transverse wave, i.e. shear wave. In the transverse wave, the particles move perpendicular to the direction of wave travel. In both longitudinal and transverse waves, the velocity of the wave is strongly affected by stress applied in the direction of particle motion. In a longitudinal wave, the direction of particle motion is the same as the direction of wave travel. In a shear wave, the direction of particle motion is perpendicular to the direction of wave travel. By using shear mode transducers mounted on opposing faces of the bearing, the acoustic velocity of a generated transverse wave will be strongly affected by the radial stress in the bearing, radial stress being the most significant component of stress in the bearing. Direct measurement of radial stress is provided from the time of flight of the transverse acoustic wave.

The time of flight required for an acoustic wave to traverse the width of a member is related to the applied load in two ways. First, as the member is loaded, the dimensions of the member will change. Thus, the time required for the signal to travel across the member will change due to changes in the length of signal travel. Second, as the member is loaded, the velocity at which the acoustic signal travels across the member will change. This is due to the stress in the member material. Therefore, knowing the relationship between the stress in the bearing, the associated change in bearing width, and the acoustic velocity will allow the stress to be calculated.

Because the time of flight is directly related to stress, as set forth above, a constant may be used to directly convert time of flight into stress. By way of example, experimental testing has determined that the time required for an acoustic signal to travel through 1 inch of American Iron and Steel Institute ("AISI") 52100 bearing steel under zero stress is 7.585 $\mu$sec. In other words, the velocity of the acoustic wave through the bearing steel is 131,839 in/sec. Experimental testing has determined that time of flight decreases by 1 nanosecond for every 3333 psi of uniaxial compressive stress applied in the direction of polarization of the acoustic shear wave. Thus, the conversion constant "K" for acoustic velocity stress in AISI 52100 bearing steel is determined to be 3333 psi/(nsec-in) or 3333 lbs/(nsec-in$^3$).

In view of the above determination of the acoustic velocity stress constant K, stress can be calculated as follows:

stress=$K \times L \times \Delta t$ where K is the acoustic velocity stress constant for the steel, L is the distance traveled by the acoustic signal across the steel, and $\Delta t$ is the time of flight of the acoustic signal.

Strain, i.e. deformation, of the steel will change the distance traveled by the acoustic signal L. The strain in the direction of wave travel due to applied stress is calculated from the modulus of elasticity and Poisson's ratio for the bearing steel, which are approximately 30×10$^6$ and 0.3, respectively. Poisson's ratio represents the proportion of strain that a material will deform in the direction perpendicular to the applied stress. Thus, under 3333 psi in the direction of principal stress, the material will strain as follows:

strain=(stress)/(modulus of elasticity)

strain=3333/30×10$^6$=0.000111 in., i.e. 111 $\mu$in.

Therefore, the strain in the direction of wave travel, which is perpendicular to the direction of principal stress is 111 $\mu$in.×0.3=0.000033 inches, i.e. 33 $\mu$in.

The time-of-flight change due to this increase in path length is 3.3×10$^{-5}$ in.×7.585 $\mu$sec/in.=2.50×10$^{-4}$ $\mu$sec Thus, the value is 0.250 nanoseconds, i.e. approximately ¼ of the 1 nanosecond change due to the applied stress. In other words, for every 3333 psi of applied stress, the time of flight decreases by approximately 1.25 nanoseconds due to stress within the steel and increases by approximately 0.25 nanosecond due to strain of the steel.

Each ultrasonic transducer, as schematically illustrated in FIG. 3, is preferably made from PZT ("lead zirconate titanate") crystals, which exhibit piezoelectric properties. The PZT crystals change their physical size under the application of an electric field. To make a transducer from a raw crystal, the crystal is polarized with respect to a direction of vibration. To polarize the crystal, an electric field is applied to the crystal under high temperature to align the piezoelectric domains.

The mode of the transducer is determined by the orientation of the polarization direction relative to the direction of travel of an acoustic wave. In a shear mode transducer, the direction of polarization is perpendicular to the lead connections, so that the crystal vibrates in a direction perpendicular to the direction of wave travel. In other words, the wave moves in the direction of lead attachment, while the particles in the wave move in the direction of polarization. More details regarding the techniques used to polarize transducers may be found in A. R. Selfridge, "The Design and Fabrication of Ultrasonic Transducers and Transducer Arrays," Ph.D. dissertation, Stanford University, 1983.

If a single, short-duration pulse is applied to the transducer, the transducer will vibrate at all frequencies present in the acoustic pulse signal. However, the amplitude of the vibration will be largest at the resonant frequency of the transducer. Moreover, the amplitude of vibration will be greatest when the resonant frequency of the transducer is close to the fundamental frequency of the acoustic pulse signal. Hence it is desirable that the fundamental pulse frequency be selected to match the resonant frequency of the transducer.

The resonant frequency of the transducer is determined primarily by transducer thickness. In general, transducer thickness is equal to one-half of the wavelength of a signal oscillating at its resonant frequency. Thus, for a 0.0055"

thick, transducer, a wavelength of 0.011" corresponds to a frequency of 16 MHz, as follows:

$$f = \frac{c}{\ddot{e}}$$

$c$ = acoustic velocity, in inches/sec
  = 4500 m/sec = $1.77 \times 10^5$ in/sec, for a PZT crystal $f$ = frequency, in Hz $\ddot{e}$ = acoustic wavelength, in inches After fabrication of the transducer, operation is verified by analyzing impedance. The resonant frequency of the transducer is then determined.

The preferred value of a transducer resonant frequency for the rolling element bearings of the present invention is 10 MHz. A transducer having a resonant frequency of 10 MHz is preferred for two reasons:

1. The size of the transducer determines its resonant frequency. A 10 MHz transducer will fit into the bearing envelope with only minor modifications to the bearing and yet be of manageable size to be easily handled and applied to the bearing surface.

2. A frequency of 10 MHz results in an acoustic wave that is fairly well-focused. That is, the acoustic wave does not spread excessively between the transmission and reception size such that its amplitude at the reception site is drastically diminished.

The duration of the pulse applied to the transducer 28a is preferably 20 nanoseconds. Thus, at a resonant frequency of 10 MHz, the duration of one full cycle of the excitation voltage of the crystal is 100 nanoseconds. Further, to excite the crystal to its full extension would require one-quarter of one full period, i.e. 25 nanoseconds. Therefore, a 20-nanosecond pulse is preferred to excite the crystal, which is just under the time required to fully excite the crystal.

The time between pulses is selected to allow any reflections which are present as oscillations in bearing race 26 to dampen before a following pulse arrives. A frequency of pulses of 500 Hz is preferred.

Once the resonant frequency is determined, a technique is then employed to determine the time of flight of the signal across a distance corresponding to the width of the race of the bearing. A variety of different signal types may be transmitted across the bearing race 26. However, the type of signal transmitted across the bearing is related to the technique used to send and receive the signal and also to the method that the time of flight is measured. In general, if a pulse is used as the type of transmitted signal, the time of flight is measured directly by triggering a timer to turn on when the signal is transmitted and to turn off when the signal is received.

Figure 4:
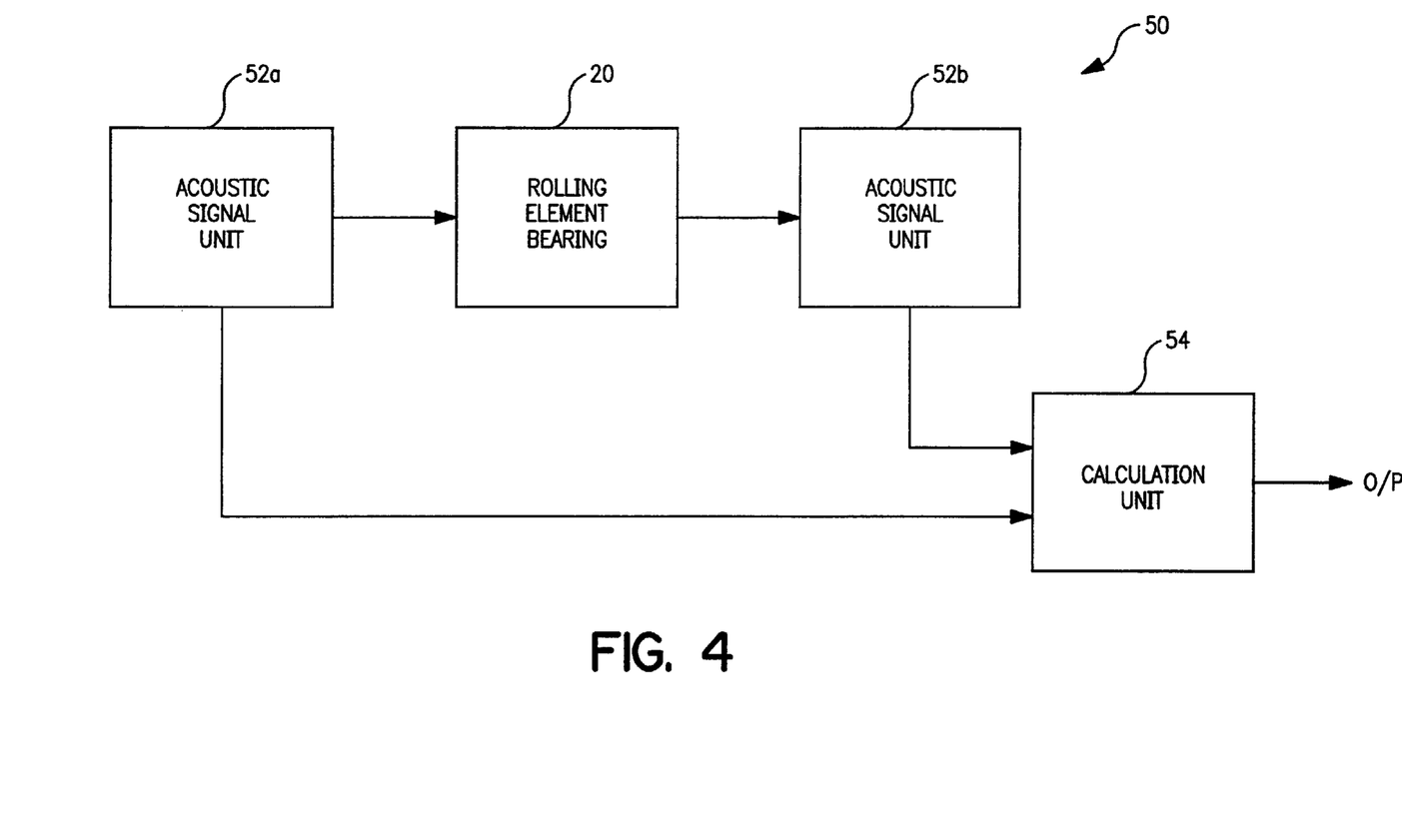
FIG. 4 is a block diagram of an apparatus to measure stress in a rolling element bearing according to an embodiment of the present invention.

FIG. 4 illustrates an apparatus 50 to measure a parameter of a rolling element bearing according to an embodiment of the present invention. In general, an acoustic signal is generated by acoustic signal unit 52a, transmitted across rolling element bearing 20, and then received by acoustic signal unit 52b. Together, acoustic signal unit 52a and acoustic signal unit 52b form acoustic signal unit 52. The acoustic signal is preferably an ultrasonic acoustic signal. Information corresponding to the time of transmission of the acoustic signal is transmitted from the acoustic signal unit 52 to calculation unit 54. Likewise, information corresponding to the time of reception of the acoustic signal is transmitted from the acoustic signal unit 52 to calculation unit 54. Together, the time of transmission and the time of reception of the acoustic signal provide time of flight information to calculation unit 54. Calculation unit 54 then calculates an output corresponding to the stress in rolling element bearing 20 from the time of flight information.

The output from calculation unit 54 may take a variety of forms, which may be recognizable by a user as indicative of stress. For example and depending upon application, the output from calculation unit 54 is an analog voltage which directly corresponds to stress. The value of the analog voltage may be directly used to indicate a level of stress or may be converted into units of stress. The conversion may be made manually through reference to a conversion table, for example during a field measurement, or may be made through connection to a computer. Alternately, the analog voltage output may be received by an analog volt meter, which has a dial indicating units of stress.

An operator during a field test would recognize a voltage level as a parameter indicating a level of stress in a bearing, and could therefore directly use this information for analysis and potential adjustment of the bearing. An example of bearing adjustment would be to adjust an amount of pre-load which is applied to the bearing.

According to an embodiment of the present invention, calculation unit 54 outputs a value of a bearing parameter, such as stress, temperature or speed. A detailed description of calculation of temperature and speed is set forth below.

Figure 5:
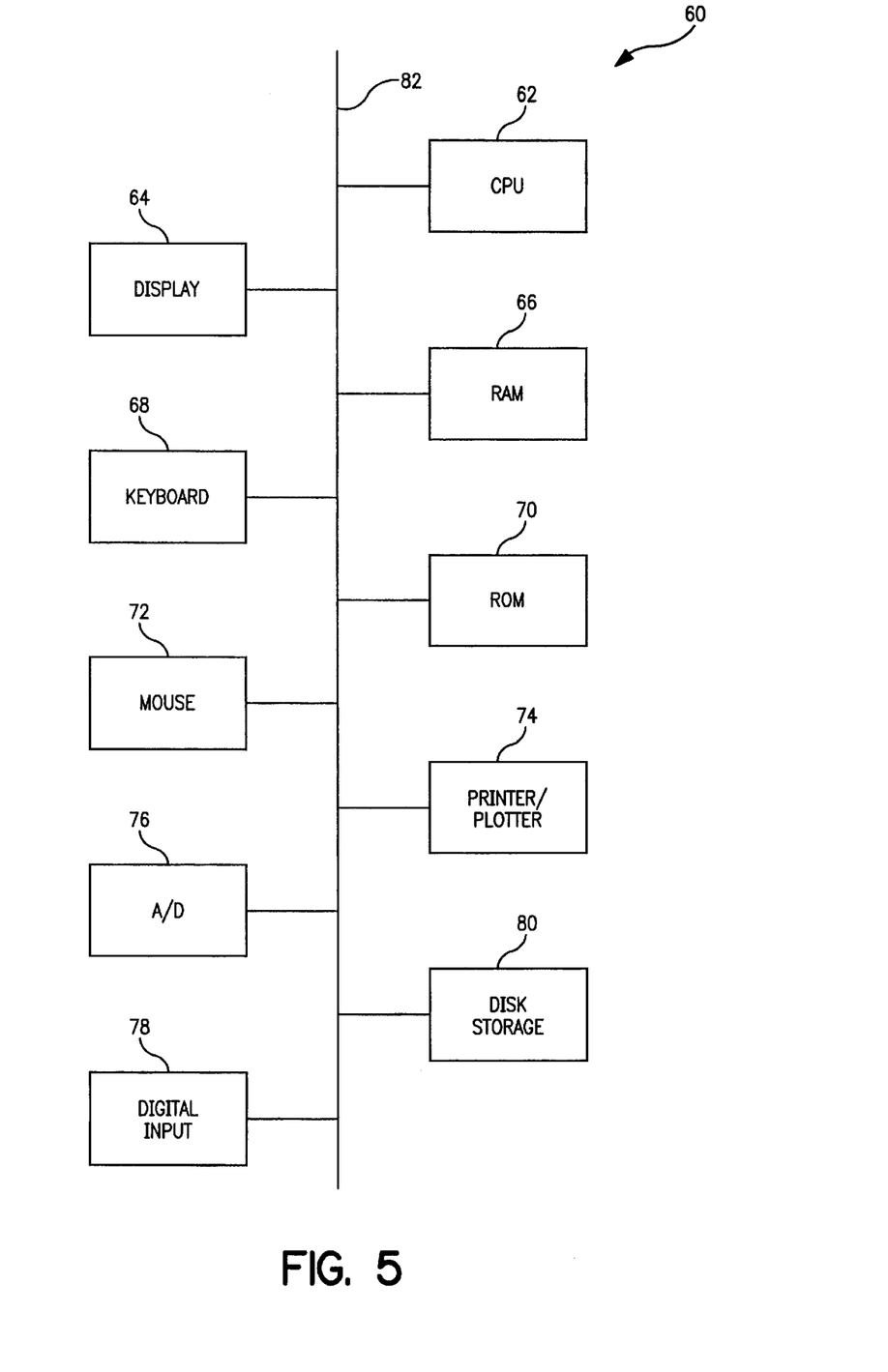
FIG. 5 is a block diagram of a computer used to calculate a stress value of a rolling element bearing.

FIG. 5 illustrates computer 60 which is used according to an embodiment of the present invention. FIG. 5 illustrates computer 60, which includes central processing unit ("CPU") 62, display 64, random access memory ("RAM") 66, keyboard 68, read only memory ("ROM") 70, mouse 72, printer/plotter 74 and analog to digital converter ("A/D") 76, digital input 78 (which may be serial or parallel), and disk storage 80. The components of computer 60 are electrically connected by data bus 82.

According to an embodiment of the present invention, time of flight information is output from acoustic signal unit 52 and is received by computer 60. Computer 60 then analyzes the information in accordance with the equations set forth above to arrive at a value of stress in desired units. The stress value is then selectively output from display 64, printer/plotter 74, or is stored in disk storage 80 for later analysis. According to different embodiments of the present invention, the time of flight information may be digital or analog when output from acoustic signal unit 52. If the time of flight information is digital, the information is received by digital input 78 of computer 82. On the other hand, if the time of flight information is analog, the time of flight information is received by A/D 76, and then converted to digital form before analysis and computation by computer 60. According to an embodiment of the present invention, the output from calculation unit 54 is input into A/D 76 for analysis by computer 60.

Figure 6:
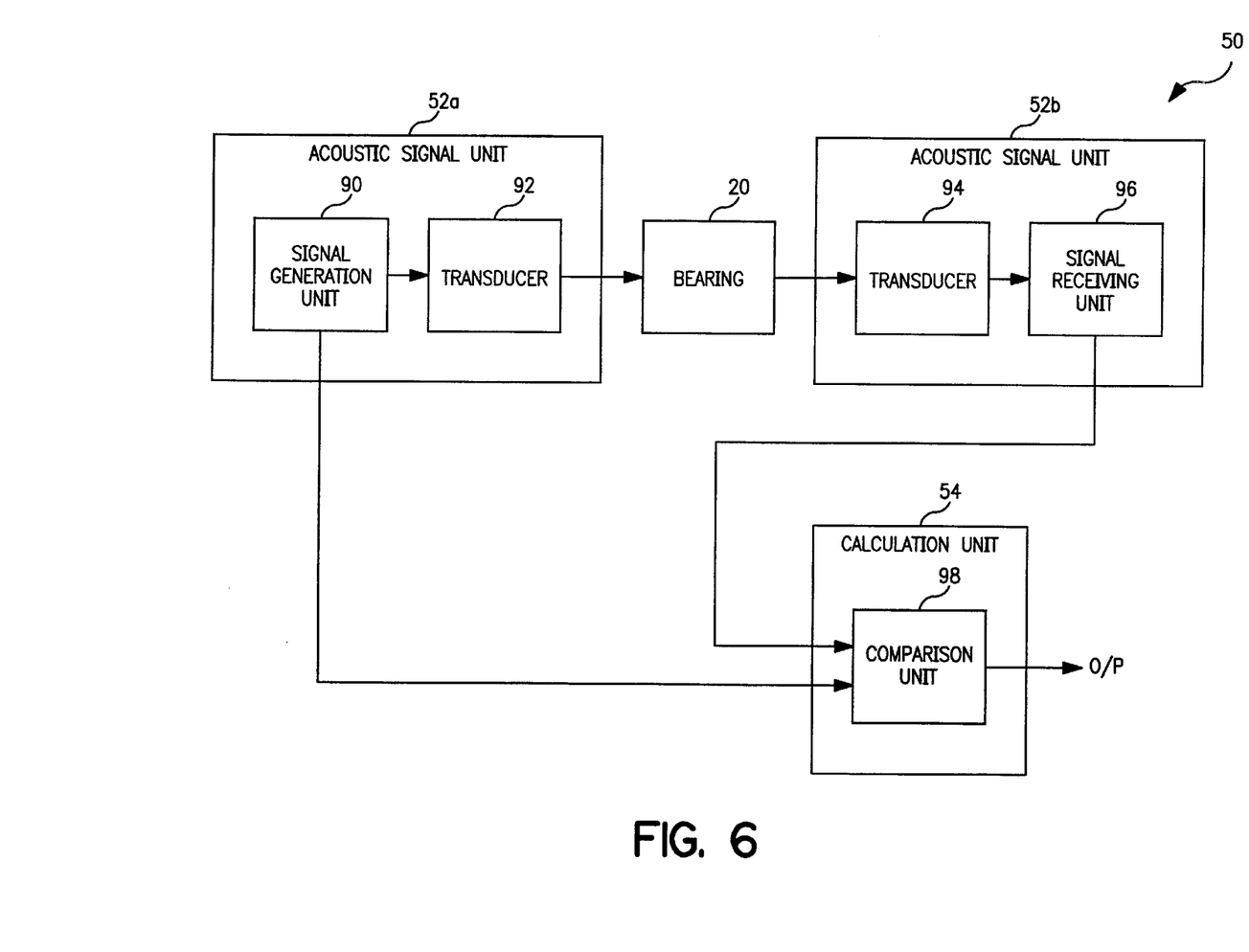
FIG. 6 is a block diagram of an apparatus to measure stress in a rolling element bearing according to an embodiment of the present invention.

FIG. 6 illustrates apparatus 50 to measure a parameter of a rolling element bearing according to another embodiment of the present invention. As illustrated, apparatus 50 includes an acoustic signal unit 52, which includes acoustic signal unit 52a and acoustic signal unit 52b. Acoustic signal unit 52a generates an acoustic signal while acoustic signal unit 52b receives the acoustic signal after transmission across bearing 20. Calculation unit 54 determines the time of flight of the acoustic signal from outputs of the acoustic signal unit 72.

As illustrated in FIG. 6, acoustic signal unit 52a includes a signal generation unit 90 generating an electrical signal and outputting the electrical signal to transducer 92. Transducer 92 is preferably a PZT piezoelectric transducer as set forth above. Transducer 92 is directly affixed to bearing 20 and generates an acoustic signal in response to the electrical signal output from signal generation unit 90. Acoustic signal unit 52b includes a transducer 94, which is affixed to bearing 20 and receives the acoustic signal transmitted across bearing 20. Transducer 94 is preferably a PZT piezoelectric transducer as set forth above. Transducer 94 converts the received acoustic signal into an electrical signal that is, in turn, received and amplified by signal receiving unit 96.

Calculation unit 54 receives a first electrical signal from signal generation unit 90, which corresponds to initiation of the acoustic signal by transducer 92. Likewise, stress calculation unit 54 receives a second electrical signal from signal receiving unit 96, which corresponds to a time of receipt of the acoustic signal by transducer 94. Stress calculation unit 54 includes a comparison unit 98 that compares each of the first and second electrical signals to determine a difference in time. The difference in time between the first and second electrical signals corresponds to a time of flight of the acoustic signal across bearing 20. According to an embodiment of the present invention, comparison unit 98 outputs a signal corresponding to the time of flight of the acoustic signal. As set forth above, the output takes the form of a voltage. According to an alternate embodiment of the present invention, the output may be digital for reading and analysis by a computer. The output corresponds to rolling element bearing parameters such as stress, temperature, and speed.

Figure 7:
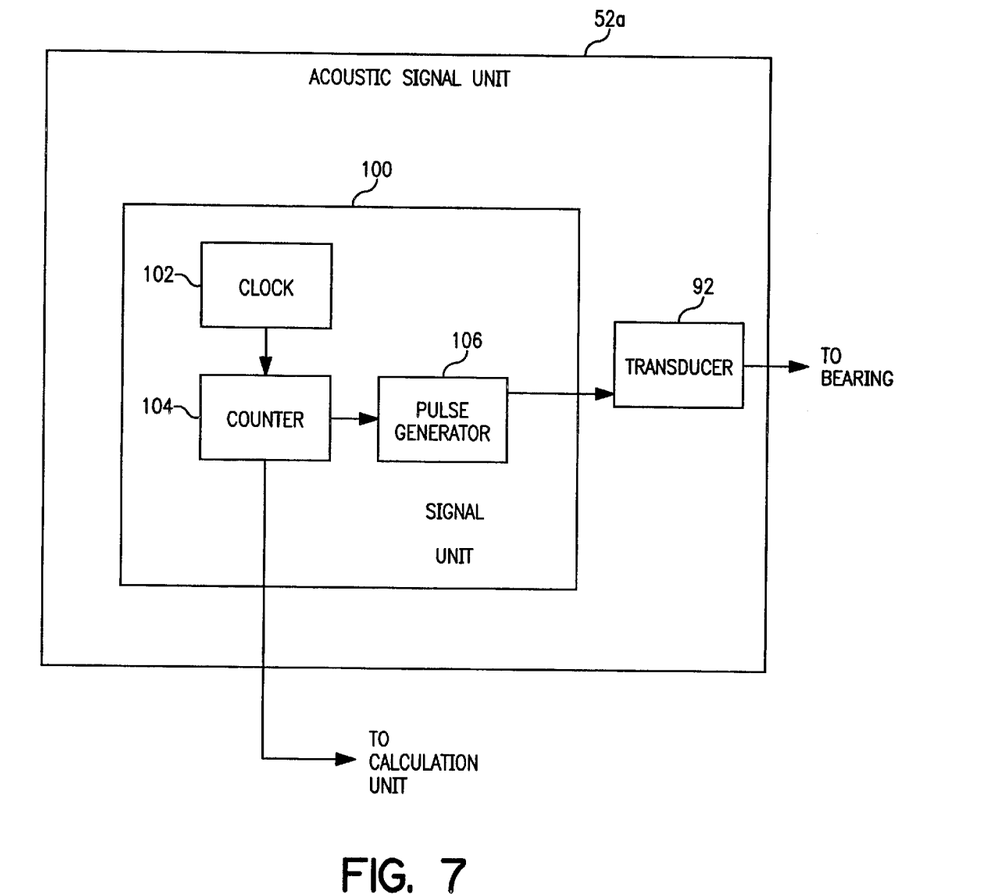
FIG. 7 is a detailed block diagram of an acoustic signal unit including a signal generation unit.
Figure 8:
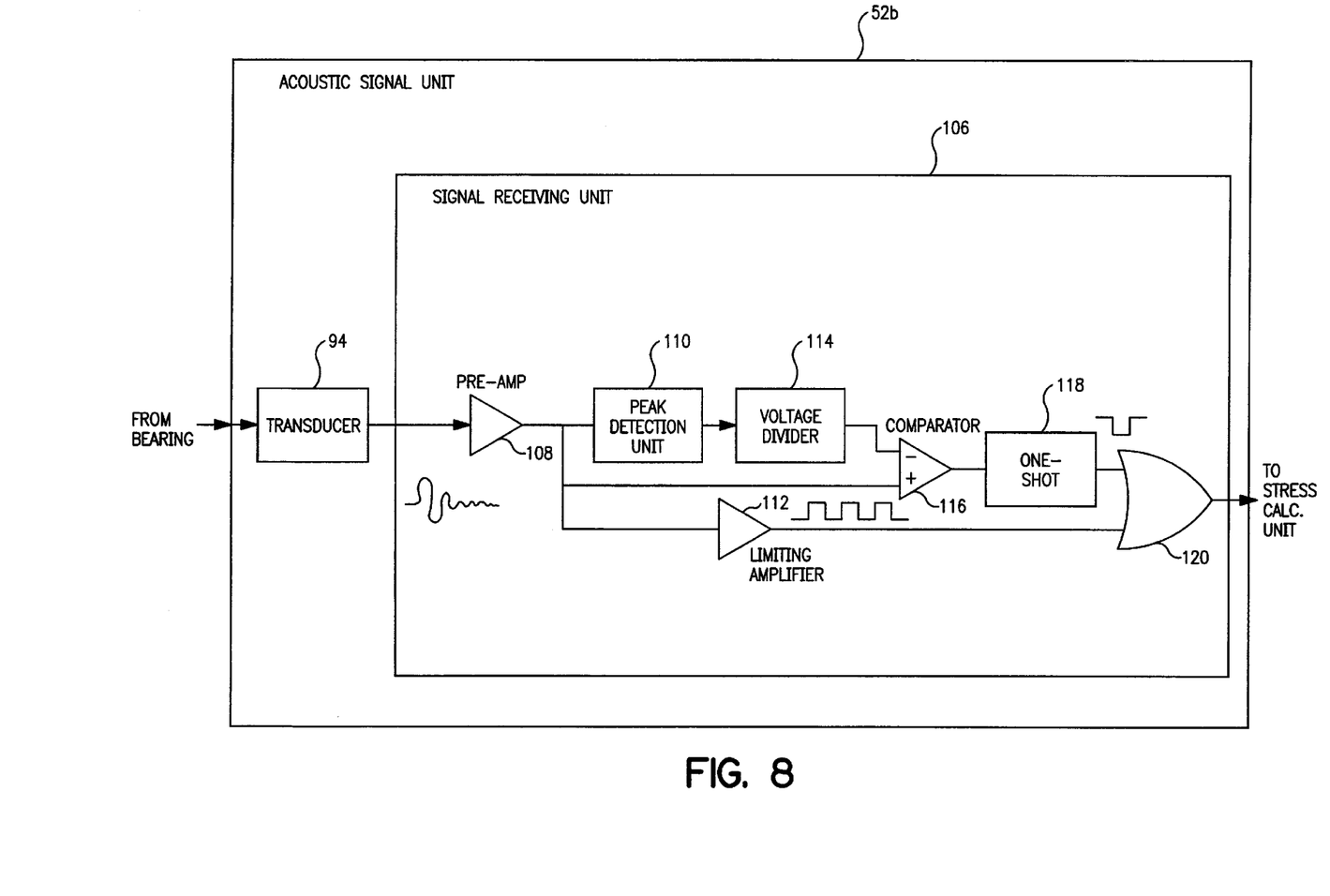
FIG. 8 is a detailed block diagram of an acoustic signal unit including a signal receiving unit.
Figure 9:
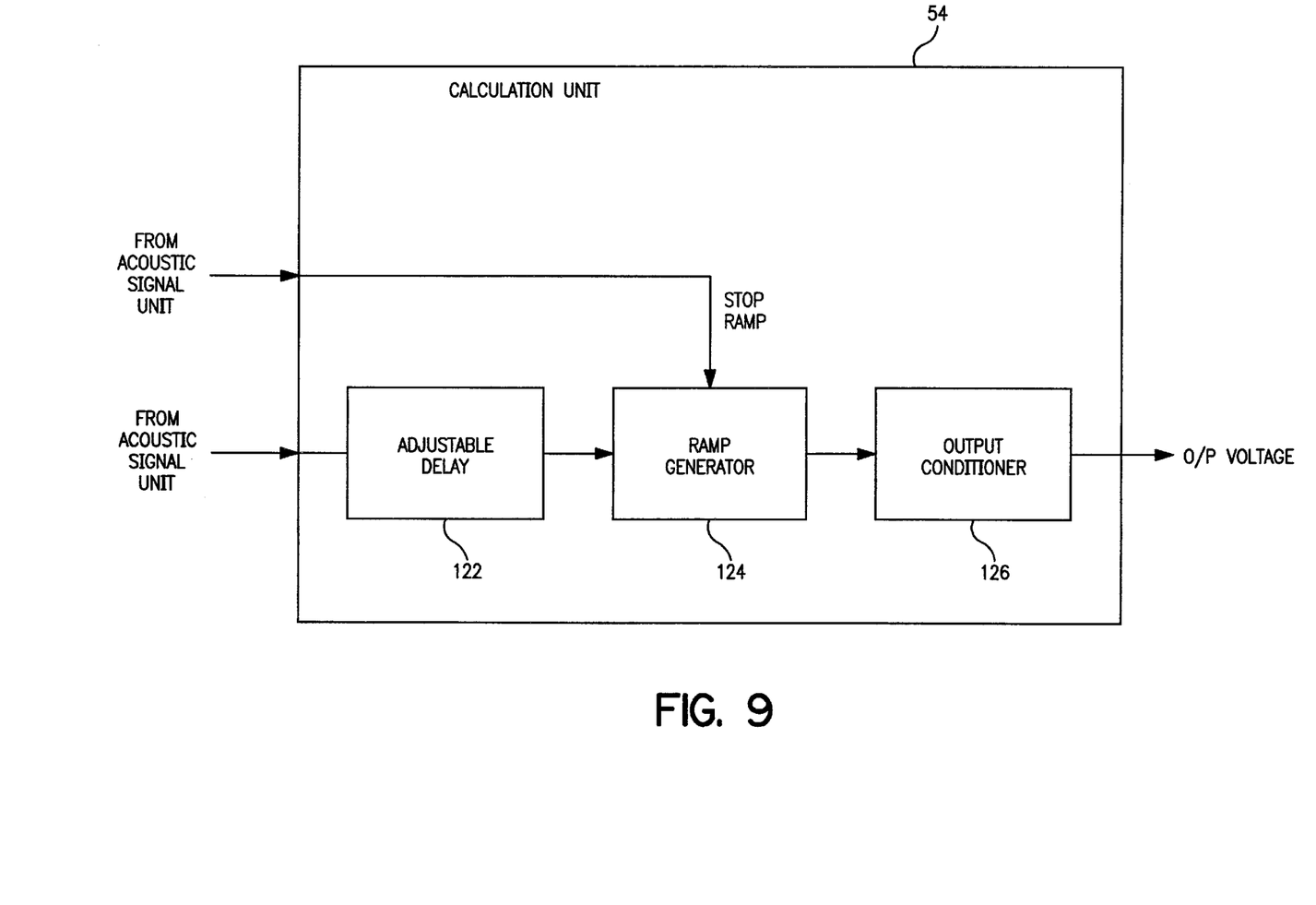
FIG. 9 is a detailed block diagram of a calculation unit.

FIGS. 7, 8, and 9 particularly illustrate detailed schematic views of acoustic signal unit 52a, acoustic signal unit 52b, and stress calculation unit 54 according to a preferred embodiment of the present invention. In general, a voltage impulse is used to drive transducer 92, which is in the form of a PZT crystal. The acoustic signal is received by transducer 94 and output as a damped sinusoidal pulse. This pulse is then processed to extract the time of occurrence of the first zero crossing subsequent to the first peak excursion of the signal since the previous measurement. The time interval between the onset of the transmit pulse and this zero crossing is then converted into a voltage output which is scaled and offset to provide high resolution of the small variations in transit time that occur as a result of applied stress.

According to FIG. 7, acoustic signal unit 52a includes signal generation unit 100 and transducer 92. Signal generation unit 100 includes clock 102, which is preferably a 20 MHz crystal oscillator. Clock 102 drives counter 104, which sets a pulse repetition rate for the system. Counter 104 generates a 40 nsec pulse, which is amplified by pulse generator 106, and then fed to transducer 92. Since transducer 92 presents a large capacitive load, a considerable amount of current is required to achieve the required voltage swing. Pulse generator 106 may be implemented with commercially available integrated circuits to provide a cost effective method for generation of the signal. In general, it is advantageous to use a smaller transducer area to minimize transducer capacitance. However, there appears to be no advantage to using a lower transmit frequency, as this will require more energy for the transmit pulse, along with the resulting uncertainty about the location of the zero crossings of the received signal. Counter 104 also outputs a signal for reception by calculation unit 54 (FIG. 9).

As illustrated in FIG. 8, acoustic signal unit 52b includes transducer 94 and signal receiving unit 106. Transducer 94 converts the received acoustic signal into an electrical signal, which in turn is amplified by pre-amp 108. Peak detection unit 110 extracts and stores the peak value output by pre-amp 108. In turn, limiting amplifier 112 creates a clipped version of the pre-amp output. Voltage divider 114 multiplies the output of peak detection unit 110 by approximately "0.65" for the reasons set forth below. Comparator 116 then compares the instantaneous value of the output from pre-amp 108 with the 0.65 value output from voltage divider 114.

Transducer 94 receives a "ringing" sine wave from bearing 20 due to successively damped oscillations of the initially transmitted acoustic signal. Because the ringing sine wave output from the receive transducer 94 is heavily damped, only the first half-cycle of the received pulse will exceed 65% of its peak value. Comparator 116 is therefore triggered only during the first half cycle of the received pulse. Comparator 116 triggers one-shot 118, which generates a short duration pulse. The short duration pulse output from one-shot 118, in combination with gate 120, masks out all zero crossings except the zero crossing immediately following the first half-cycle of the received pulse. Pulse echoes and background noise have substantially lower amplitude than the primary received pulse and are therefore ignored by the system. Gate 120 then outputs the signal to calculation unit 54.

FIG. 9 illustrates calculation unit 54 according to an embodiment of the present invention. Calculation unit 54 includes adjustable delay 122, ramp generator 124, and output conditioner 126. A user sets adjustable delay 122 to be slightly less than an expected transit time of an acoustic signal pulse. At the end of the delay period, ramp generator 124 is triggered. Ramp generator 124 uses a current source to charge a capacitor at a controlled rate. The voltage ramp on the capacitor continues until a signal is asserted by gate 120, corresponding to the arrival of the targeted zero crossing of the received pulse. The value of the voltage ramp is then held until just prior to the start of the next ramp, when it is rapidly reset to zero to prepare for the next ramp. Output conditioning circuit 126 then scales, offsets, and buffers the ramp voltage for use by other instrumentation.

In accordance with the preferred embodiment of the present invention, with particular reference to FIGS. 7, 8 and 9, the apparatus produces a pulse with a transit time of 500 nsec to produce an output range of 20 volts. Noise at the output is observed to be less than 0.4 millivolts RMS, corresponding to 10 psec RMS noise referred to the input.

Figure 10:
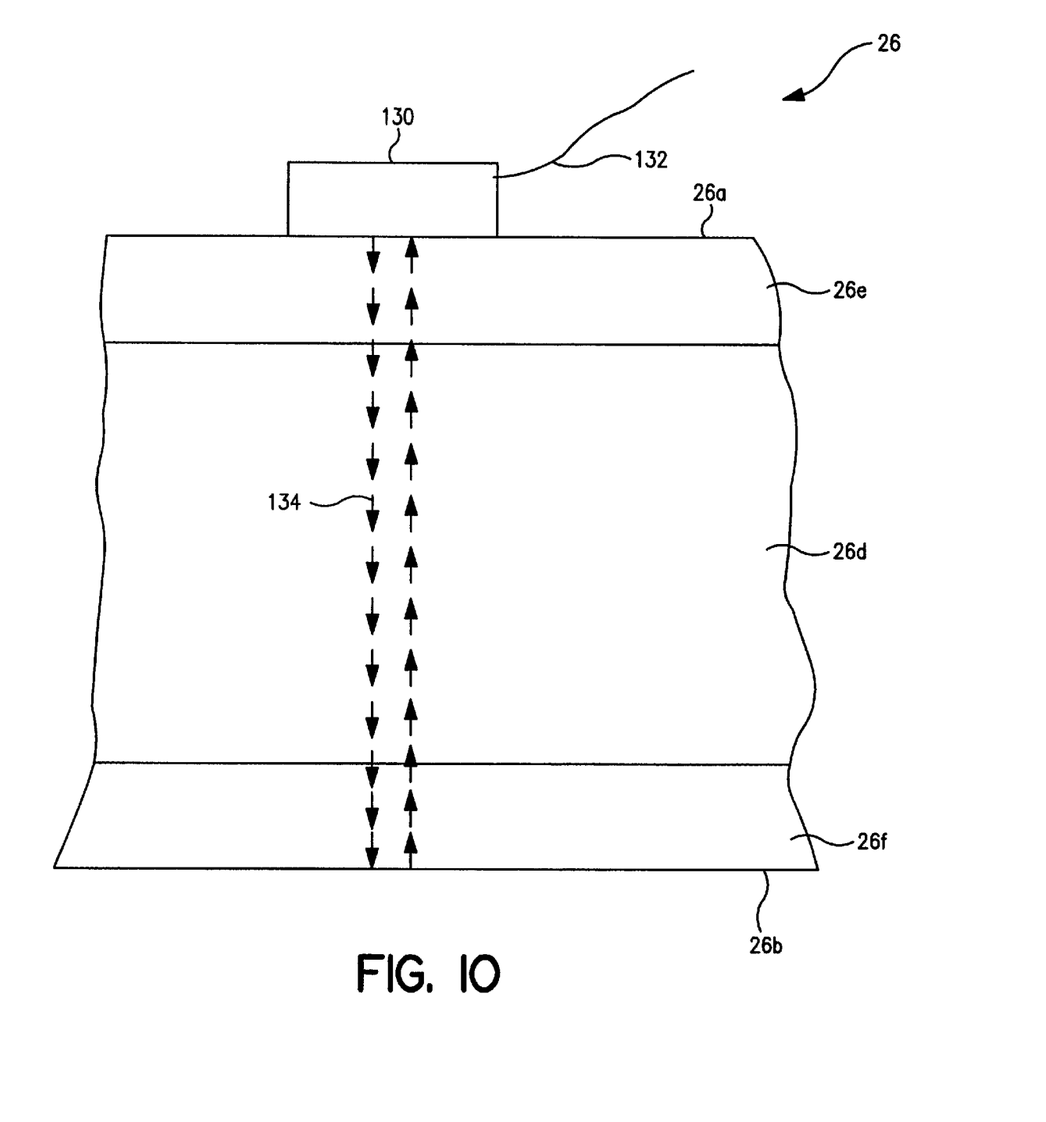
FIG. 10 is a sectional view of a bearing race supporting a single transducer for ultrasonic stress measurement.

FIG. 10 is a schematic view of bearing race 26 supporting a single transducer 130 according to another embodiment of the present invention. According to the illustrated embodiment, the time of flight of an acoustic pulse across the bearing race 26 is measured according to a pulse-echo method. The pulse-echo employs the use of a single transducer 130, which is preferably a PZT piezoelectric crystal. By transmitting and receiving the signals from the same side of the bearing, a single electrical connection 132 is used.

According to the pulse-echo method, illustrated in FIG. 10, an acoustic signal pulse 134 is transmitted from a transducer 130 and is reflected from second face 26b of bearing race 26. The time required for signal propagation is then divided by two to determine the time of flight across a distance corresponding to the width of the bearing race 26.

Figure 11:
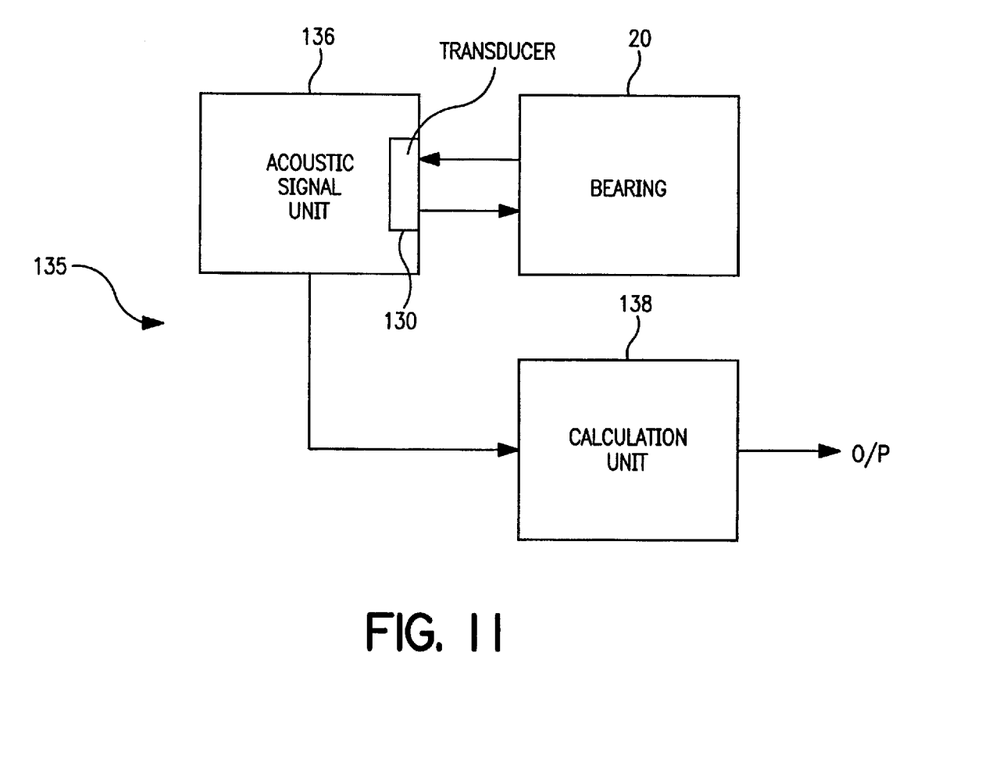
FIG. 11 is a block diagram of an apparatus to measure stress in a rolling element bearing using a single transducer.

FIG. 11 illustrates apparatus 135 to measure stress in a rolling element bearing according to an embodiment of the present invention. Apparatus 135 includes an acoustic signal unit 136, which includes transducer 130. Acoustic signal unit 136 generates an acoustic signal and receives the reflected acoustic signal from bearing 20. Thus, the time of flight of the acoustic signal across a distance corresponding to the width of the bearing race is equal to one half of the time difference between the transmitted pulse and the received pulse. The time information is outputted to calculation unit 138, which produces an output value indicating stress in bearing 20. The output value may be analog or digital and may be interpreted directly, or used with analysis by a computer. A detailed description of the components used to generate and detect the acoustic signal from bearing 20 are previously disclosed above with reference to FIGS. 7, 8, 9. An understanding thereof is readily known by those skilled in the art, and further description is suitably omitted.

Many bearing parameters may be determined from an ultrasonic acoustic signal. Stress determination is set forth above. Other bearing parameters that may be determined from an ultrasonic acoustic signal include temperature and speed.

Temperature is an important parameter for rolling element bearings. The velocity of the acoustic signal and, to a lesser extent, the size of the bearing component, are affected by the temperature of the component as well as its state of stress. However, the quantity of stress changes periodically due to the passage of rolling elements over the bearing race. Therefore, the output will have a cyclical change with respect to a base level, i.e. a DC level. The cyclical change therefore is the stress from rolling element passage, which is one parameter of interest, while the base level represents the stress in the component under zero applied load as well as its current temperature. Changes in the base level, i.e. DC offset, are output from a stress calculation unit to provide temperature information of the bearing.

In short, the DC component changes with temperature, and the AC component changes with stress. Temperature is an important operating parameter in bearings, and provides information regarding the health of operation. Temperature information may be used to provide an indication that the bearing is being improperly used or is approaching a dangerous and potentially life-threatening condition. As such, knowledge of the operating temperature can be used in a number of important ways. It may be used in conjunction with a stress measurement to assess the suitability of the application for the bearing under use. Alternately, temperature information may be used to alert the user to the need for an alteration of the operating condition that may be causing damage to the bearing or to perform maintenance on the bearing.

Speed is also an important parameter for rolling element bearings. The frequency of rolling element passes in the rolling element bearing, i.e. the frequency of the stress changes, is directly related to the speed of the bearing, and therefore provides additional information related to bearing analysis. Bearing speed may therefore be directly calculated from the frequency of rolling element passes and bearing geometry.

As set forth above, the time of flight measurement may be used to determine a number of important real-time operating parameters in bearings, including, but not limited to stress (and from this, load), temperature and speed.

Rolling element loads may be determined from time of flight measurement of an acoustic signal. By performing a calibration procedure, as set forth in Rhodes, et al., U.S. Pat. No. 5,952,587, the bearing rolling element loads may be inferred directly from the above-described stress measurement. Thus, the calibration procedure from Rhodes, et al. is applied to the determined stress in the bearing to thereby determine load. Rolling element loads are useful in assessing the suitability of the application for the bearing under use, monitoring and observing changes in the bearing load distribution, assessing the structure supporting the bearing, and determining the loads in the equipment in which the bearing is installed, or system loads. Knowledge of the system loads can be used to monitor and control the process being performed by the equipment in which the bearing is installed.

The foregoing is considered as illustrative only of the principles of the invention, and since numerous modifications and changes will readily occur to those skilled in the art, it is not desired to limit the invention to the exact construction and operation shown and described, and accordingly, all suitable modifications and equivalents may be resorted to, falling within the scope of the present invention.

Having described the invention, what is claimed is:

1. An apparatus to measure stress in a rolling element bearing, comprising:

an acoustic signal unit to transmit an acoustic signal across the rolling element bearing, to receive the acoustic signal, and to output information corresponding to a time of flight of the acoustic signal, said acoustic signal unit comprising a signal generation unit to generate a first electrical signal, a first transducer to generate the acoustic signal in response to the first electrical signal, and a second transducer to generate a second electrical signal in response to the received acoustic signal; and a calculation unit to calculate stress in the rolling element bearing from the outputted information, said calculation unit comprising a comparison unit to compare the first and second electrical signals to determine the time of flight of the acoustic signal, wherein the time of flight corresponds to the stress in the rolling element bearing, said comparison unit calculating the stress according to the formula $$\text{stress} = K \times L \times \Delta t$$

wherein K is the acoustic velocity stress constant for the rolling element bearing, L is the distance traveled by the acoustic signal across the rolling element bearing, and $\Delta t$ is the time of flight of the acoustic signal across the rolling element bearing.

2. The apparatus to measure stress in a rolling element bearing according to claim 1, wherein said first and second transducers are affixed to alternate sides of a race of the rolling element bearing.

3. The apparatus to measure stress in a rolling element bearing according to claim 1, wherein said first and second transducers are affixed to alternate sides of a race of the rolling element bearing with epoxy resin.

4. The apparatus to measure stress in a rolling element bearing according to claim 1, wherein said first and second transducers are affixed to alternate sides of a bearing race of the rolling element bearing, the bearing race being one of the group consisting of an inner bearing race and an outer bearing race.

5. The apparatus to measure stress in a rolling element bearing according to claim 1, said acoustic signal unit generating a first electrical signal, and comprising a transducer affixed to a side of a race of the rolling element bearing to generate an acoustic signal in response to the first electrical signal, wherein said transducer generates a second electrical signal in response to receipt of a reflection of the generated acoustic signal, and outputs the second electrical signal.

6. The apparatus to measure stress in a rolling element bearing according to claim 5, said calculation unit to receive and compare the first and second electrical signals to determine a difference in time, wherein the difference in time corresponds to twice the time of flight of the acoustic signal across the rolling element bearing, and the time of flight corresponds to the stress in the bearing.

7. The apparatus to measure stress in a rolling element bearing according to claim 5, wherein said transducer is affixed to a side of a race of the rolling element bearing.

8. The apparatus to measure stress in a rolling element bearing according to claim 7, wherein the race is one of the group consisting of an inner bearing race and an outer bearing race.

9. The apparatus to measure stress in a rolling element bearing according to claim 1, said calculation unit comprising a comparison unit to compare time of transmission and time of reception of the acoustic signal to determine the time of flight of the acoustic signal across the rolling element bearing as the outputted information, wherein the time of flight corresponds to the stress in the rolling element bearing.

10. The apparatus to measure stress in a rolling element bearing according to claim 1, wherein the acoustic signal is an ultrasonic acoustic signal.

11. An apparatus to measure stress in a rolling element bearing, comprising:
an acoustic signal unit to transmit an acoustic signal across the rolling element bearing, to receive the acoustic signal, and to output information corresponding to a time of flight of the acoustic signal, said acoustic signal unit comprising a signal generation unit to generate a first electrical signal, a first transducer to generate the acoustic signal in response to the first electrical signal, and a second transducer to generate a second electrical signal in response to the received acoustic signal; and
a calculation unit to calculate stress in the rolling element bearing from the outputted information, said calculation unit comprising a comparison unit to compare the first and second electrical signals to determine the time of flight of the acoustic signal, wherein the time of flight corresponds to the stress in the rolling element bearing, said comparison unit calculating the stress by multiplying the acoustic time constant for the rolling element bearing by the distance traveled by the acoustic signal across the rolling element bearing, and by the time of flight determined by said comparison unit.

12. An apparatus to measure stress in a rolling element bearing, comprising:
an acoustic signal unit to transmit an acoustic signal across the rolling element bearing, to receive the acoustic signal, and to output information corresponding to a time of flight of the acoustic signal, said acoustic signal unit generating a first electrical signal, and comprising a transducer affixed to a side of a race of the rolling element bearing to generate an acoustic signal in response to the first electrical signal, wherein said transducer generates a second electrical signal in response to receipt of a reflection of the generated acoustic signal, and outputs the second electrical signal; and
a calculation unit to calculate stress in the rolling element bearing from the outputted information, said calculation unit calculating the stress by multiplying the acoustic time constant for the rolling element bearing by the distance across the rolling element bearing, and by the time of flight of the acoustic signal across the rolling element bearing.

13. A method of measuring stress in a rolling element bearing, comprising:
transmitting an acoustic signal across the rolling element bearing;
receiving the transmitted acoustic signal from rolling element bearing;
determining a time of flight of the acoustic signal across the rolling element bearing from the time of transmission and the time of reception; and
calculating stress in the rolling element bearing from the determined time of flight, wherein the stress is calculated according to the formula $$stress = K \times L \times \Delta t$$

wherein K is the acoustic velocity stress constant for the rolling element bearing, L is the distance traveled by the acoustic signal across the rolling element bearing, and $\Delta t$ is the time of flight across the rolling element bearing.

14. The method of measuring stress in a rolling element bearing according to claim 13, further comprising:
generating a first electrical signal;
generating the acoustic signal in response to the first electrical signal;
generating a second electrical signal in response to the received acoustic signal; and
comparing the first and second electrical signals to determine a difference in time, wherein the difference in time corresponds to the time of flight of the acoustic signal across the rolling element bearing.

15. The method of measuring stress in a rolling element bearing according to claim 13, further comprising:
generating a first electrical signal;
generating the acoustic signal in response to the first electrical signal;
generating a second electrical signal in response to a reflection of the generated acoustic signal across the rolling element bearing; and
comparing the first and second electrical signals to determine a difference in time, wherein the difference in time corresponds to two times the time of flight of the acoustic signal across the rolling element bearing.

16. The method of measuring stress in a rolling element bearing according to claim 13, wherein the acoustic signal is an ultrasonic acoustic signal.

17. An apparatus to measure stress in a rolling element bearing, comprising:
a signal generation unit to generate a first electrical signal;
a first transducer affixed to a race of the rolling element bearing to generate an acoustic signal in response to the first electrical signal;
a second transducer affixed to the race of the rolling element bearing alternate from said first transducer to generate a second electrical signal in response to the received acoustic signal; and
a comparison unit to compare the first and second electrical signals to determine a difference in time, wherein the difference in time corresponds to a time of flight of the acoustic signal across the rolling element bearing, and the time of flight corresponds to the stress in the rolling element bearing, said comparison unit calculating the stress by multiplying the acoustic time constant for the race of the rolling element bearing by the distance traveled by the acoustic signal across the race, and the difference in time determined by said comparison unit.

18. An apparatus to measure a parameter of a rolling element bearing, comprising:

an acoustic signal unit to transmit an acoustic signal across the rolling element bearing, to receive the acoustic signal, and to output information corresponding to a time of flight of the acoustic signal; and a calculation unit to calculate a parameter of the rolling element bearing from the outputted information, wherein the parameter is stress in the rolling element bearing, and wherein bearing element loads are inferred from the stress parameter.

19. A method of measuring a parameter of a rolling element bearing, comprising:

transmitting an acoustic signal across the rolling element bearing;

receiving the transmitted acoustic signal from rolling element bearing;

determining a time of flight of the acoustic signal from the time of transmission and the time of reception; and calculating a parameter of the rolling element bearing from the determined time of flight, wherein bearing element loads are inferred from the stress parameter.

20. An apparatus to measure stress in a rolling element bearing, comprising:

a signal generation unit to generate a first electrical signal;

a first transducer affixed to a race of the rolling element bearing to generate an acoustic signal in response to the first electrical signal;

a second transducer affixed to the race of the rolling element bearing alternate from said first transducer to generate a second electrical signal in response to the received acoustic signal; and a comparison unit to compare the first and second electrical signals to determine a difference in time, wherein the difference in time corresponds to a time of flight of the acoustic signal across the rolling element bearing, and the time of flight corresponds to the stress in the rolling element bearing, wherein said comparison unit calculates the stress by multiplying the acoustic time constant for the rolling element bearing by the distance traveled by the acoustic signal across the rolling element bearing, and by the difference in time determined by said comparison unit.

* * * * *